(12) United States Patent
Shikata et al.

(10) Patent No.: US 7,820,577 B2
(45) Date of Patent: *Oct. 26, 2010

(54) BIOMEDICAL MEMBER AND METHOD FOR PRODUCING THE SAME

(75) Inventors: Kunihide Shikata, Kirishima (JP); Takefumi Nakanishi, Gamo-cho (JP); Yucong Wang, Kirishima (JP)

(73) Assignee: Kyocera Corporation, Kyoto (JP)

( * ) Notice: Subject to any disclaimer, the term of this patent is extended or adjusted under 35 U.S.C. 154(b) by 927 days.

This patent is subject to a terminal disclaimer.

(21) Appl. No.: 10/578,025

(22) PCT Filed: Oct. 29, 2004

(86) PCT No.: PCT/JP2004/016128

§ 371 (c)(1),
(2), (4) Date: Dec. 27, 2006

(87) PCT Pub. No.: WO2005/042047

PCT Pub. Date: May 12, 2005

(65) Prior Publication Data

US 2008/0275568 A1    Nov. 6, 2008

(30) Foreign Application Priority Data

Oct. 30, 2003 (JP) ............... 2003-370208
Dec. 25, 2003 (JP) ............... 2003-431558
Jan. 28, 2004 (JP) ............... 2004-020564

(51) Int. Cl.
C04B 35/48 (2006.01)
C04B 35/00 (2006.01)
B32B 9/00 (2006.01)

(52) U.S. Cl. ............... 501/105; 501/103; 501/127; 428/469; 428/472; 428/472.2

(58) Field of Classification Search ......... 501/102–105, 501/127, 153; 428/469, 471, 472, 472.2, 428/689
See application file for complete search history.

(56) References Cited

U.S. PATENT DOCUMENTS 4,772,576 A    9/1988    Kimura et al.
(Continued)

FOREIGN PATENT DOCUMENTS

CN    1081175 C    3/2002
(Continued)

OTHER PUBLICATIONS

Ryoichi Shikata et al., "Mechanical Properties and Characterization of $ZrO_2$-$Al_2O_3$ Composites with High Fracture Strength", Japan Society of Powder and Powder Metallurgy; Apr. 10, 1991; vol. 38, No. 3 pp. 57-61.

(Continued)

*Primary Examiner*—Karl E Group
*Assistant Examiner*—Noah S Wiese
(74) *Attorney, Agent, or Firm*—Hogan Lovells US LLP (57) ABSTRACT

A biomedical member having high strength, high toughness and high hardness and an artificial joint that uses the same are provided. In addition, a biomedical member that exhibits high wear resistance even in in vivo environment and an artificial joint are provided.

Such a composite ceramic is used that contains 65% by weight or more $Al_2O_3$, 4 to 34% by weight of $ZrO_2$ and 0.1 to 4% by weight of SrO, while Sr forms a solid solution with part of the $ZrO_2$ grains. The composite ceramics further contains $TiO_2$, MgO and $SiO_2$ as sintering additives, while controlling the amounts to 0.20% by weight or more $SiO_2$, 0.22% by weight or more $TiO_2$ and 0.12% by weight or more MgO, and the total amount of $SiO_2$, $TiO_2$ and MgO within a range from 0.6 to 4.5% by weight.

13 Claims, 3 Drawing Sheets

U.S. PATENT DOCUMENTS

| | | | |
|---|---|---|---|
| 5,285,078 A | | 2/1994 | Mimura et al. |
| 5,403,795 A | | 4/1995 | Koyama et al. |
| 5,525,560 A | * | 6/1996 | Yamazaki et al. ........... 501/103 |
| 5,686,366 A | | 11/1997 | Koyama et al. |
| 7,148,167 B2 | * | 12/2006 | Shikata et al. ............. 501/105 |
| 2002/0010070 A1 | * | 1/2002 | Cales et al. ................ 501/105 |
| 2002/0198602 A1 | | 12/2002 | Nawa et al. |

FOREIGN PATENT DOCUMENTS

| | | | |
|---|---|---|---|
| EP | 1228774 A1 | | 8/2002 |
| GB | 2270687 A | | 3/1994 |
| JP | 60-204666 | | 10/1985 |
| JP | 03-151978 | | 6/1991 |
| JP | 05-206514 | | 8/1993 |
| JP | 05-294718 | | 11/1993 |
| JP | 06-022572 | | 3/1994 |
| JP | 06-172026 | | 6/1994 |
| JP | 09-221354 | | 8/1997 |
| JP | 2000-016836 | | 1/2000 |
| JP | 2000-159568 | | 6/2000 |
| JP | 2000-191372 | | 7/2000 |
| JP | 2000-191372 A | * | 7/2000 |
| JP | 2003-040673 | | 2/2003 |

OTHER PUBLICATIONS

R.Z. Chen et al., "Toughening alumina with both nickel and zirconia inclusions" Journal of the European Ceramic Society, vol. 20, No. 12, pp. 1901-1906, Nov. 2000.

O. Sbazero et al., "R-curve behavior of alumina toughened with molybdenum and zirconia particles" Materials Science & Engineering, vol. A359, pp. 297-302, Oct. 2003.

Japanese language office action dated May 18, 2010 and its English language translation for corresponding Japanese application 2003370208.

* cited by examiner

BIOMEDICAL MEMBER AND METHOD FOR PRODUCING THE SAME

CROSS-REFERENCE TO THE RELATED APPLICATIONS

This application is a national phase of a PCT application No. PCT/JP2004/016128 filed Oct. 29, 2004, the entire contents of which are incorporated by reference. This application also claims benefit of priority to Japanese Patent Application No. 2003-370208 filed Oct. 30, 2003, Japanese Patent Application No. 2003-431558 filed Dec. 25, 2003 and 2004-020564 filed Jan. 28, 2004, the entire contents of all incorporated by reference.

BACKGROUND OF THE INVENTION

1. Field of the Invention

The present invention relates a biomedical member made of sintered ceramics, a method for producing the same and an artificial joint.

2. Description of the Related Art

Alumina-based ceramics and zirconia-based ceramics are bio-inactive materials and have excellent properties such as high mechanical strength and high wear resistance, and therefore have been used in medical applications such as artificial joint and artificial dental implant. In order to make an artificial hip joint, for example, a ceramic is used to form the head and an ultra-high molecular polyethylene is used to form the acetabulum socket, because the combination of alumina-based or zirconia-based ceramics and ultra-high molecular polyethylene is less susceptible to wearing and damage than in the case of metals (for example, refer to Japanese Patent Examined Publication No. 6-22572).

An artificial hip joint having sliding members both formed from alumina-based ceramics has also be developed (for example, refer to Japanese Unexamined Patent Publication (Kokai) No. 2000-16836).

Much attention has also been paid to a composite ceramic formed from alumina and zirconia mixed in predetermined amounts, since such a material achieves higher strength than those of individual ceramics, due to the effect of forming fine crystal grains (for example, refer to Ryoichi SHIKATA et al. "Mechanical Properties and Characterization of $ZrO_2$—$Al_2O_3$ Composites with High Fracture Strength", Japan Society of Powder and Powder Metallurgy; Apr. 10, 1991; Vol. 38, No. 3, pp. 57-61).

For the purpose of reducing the production cost or improving the property of the composite material described above, researches have been conducted on adding small amounts of additional components. For example, it has been disclosed to make it possible to sinter dense material at a lower temperature by adding $SiO_2$, MgO and CaO to a composition containing 70% by weight or more alumina, thereby to make a material having excellent wear resistance at a low production cost (for example, refer to Japanese Unexamined Patent Publication (Kokai) No. 5-206514 and Japanese Unexamined Patent Publication (Kokai) No. 9-221354).

It has also been disclosed to produce alumina-zirconia composite material having high toughness, by adding an oxides of the group 5A metal of the Periodic Table and $SiO_2$ together, thereby making use of the effect of accelerating the anisotropic growth (for example, refer to Japanese Unexamined Patent Publication (Kokai) No. 2000-159568).

Alumina-based ceramics is an excellent biomedical member, but is far inferior to zirconia-based ceramics with regards to strength and toughness. In the case of an artificial hip joint that has a sliding interface between alumina-based ceramics members, for example, cases of patients whose artificial hip joint were broken due to insufficient strength and toughness of alumina-based ceramics have been reported.

Zirconia-based ceramics has higher strength and higher toughness than alumina-based ceramics, but is susceptible to phase transition in an in vivo environment containing abundant water, thus resulting in poor surface roughness. Poor surface roughness leads to wear in the sliding surfaces thereby generating particle of the worn ceramic. When the particle of the worn ceramic is accumulated in the body tissues of a patient around the artificial hip joint, bone resorption takes place. The bone resorption causes loosening between the artificial hip joint and the bone. Generation of the wear particle occurs particularly conspicuously in the sliding interface between zirconia-based ceramics members.

With regards to the composite material described above, it is known that fracture toughness is improved but strength and hardness are caused to decrease by the generation of grains having shape anisotropy. While improving the fracture toughness requires it to grow the grains having shape anisotropy in elongated shapes, strength and hardness decrease as the grains grow larger. According to Japanese Unexamined Patent Publication (Kokai) No. 2000-159568, while anisotropic growth of alumina grains showed the effect of improving the toughness, bending strength decreased to 1050 MPa or lower, indicating that the growth of grains having shape anisotropy resulted in a decrease in strength. Therefore, it is necessary to study a method for improving toughness while suppressing the crystal grains from growing, in order to obtain a material having high strength and high toughness.

SUMMARY OF THE INVENTION

The present invention has been contrived in order to solve the problems described above, and has an object of providing a biomedical member that has high strength and high toughness, a method for producing the same and an artificial joint.

The inventors of the present application found that growth of crystal grains can be effectively suppressed during sintering, by adding predetermined quantity of sintering additives to a raw material including $Al_2O_3$ and $ZrO_2$ containing alumina as the main component, and that the sintered material shows high strength superior to the conventional materials, thereby completed the present invention.

The biomedical member of the present invention is a composite ceramic including an alumina phase and a zirconia crystal phase wherein a mean grain size of the zirconia crystal phase is 0.5 μm or smaller and the biomedical member contains a metal phase such as Mo, W or a mixture of Mo and W or metal oxide phase consisting of SrO or $Y_2O_3$ and sintering additives.

First invention, in particular, is a biomedical member made of composite ceramics that includes of zirconia crystal phase containing 2.8 to 4.5 mol % of $Y_2O_3$ and metal phase of either Mo or W or a mixture of Mo and W, wherein a mean grain size of the zirconia crystal phase is 0.35 μm or smaller, mean grain size of the metal phase is 1 μm or smaller, the amount of the metal phase is from 5 to 25% by weight, and 95% or more of the metal phase exists in the grain boundaries of the zirconia crystal phase.

In such a constitution, since the mean grain size of the zirconia crystal phase that constitutes the composite ceramics is smaller than that of the metal phase, growth of crystal grains is suppressed due to the difficulty to contain a part of the metal phase into the zirconia crystal phase. Wear resistance test of such a composite ceramic shows that the zirconia crystal phase is suppressed from sloughed off and, if sloughed-off occurs, it is restricted to a portion of a small volume and therefore keeps the rate of wear at a low level, thus resulting in higher wear resistance.

In the composite ceramics described above, it is preferable that alumina phase having a mean grain size of 0.5 µm or smaller is contained in the grain boundaries of the zirconia crystal phase and the metal phase. By containing alumina phase that has higher hardness than the zirconia crystal phase in the grain boundaries that is the boundaries where sloughed-off of crystal phase takes place, it is made possible to improve the wear resistance further.

It is preferable that the composite ceramics described above contains the alumina phase in the amount of 30% by weight or less.

According to the first invention, a biomedical member having high strength and high toughness can be provided. The composite ceramics has excellent sliding property as deterioration of surface properties caused by phase transition does not occur even in in vivo environment where water exists in abundance. Accordingly, the biomedical member of the present invention demonstrates high wear resistance also when used as a sliding member. Therefore, an artificial joint having high strength, high toughness and high wear resistance can be made by constituting sliding members of the artificial joint, that move while rubbing against each other, from the composite ceramics.

Second invention is based on the fact that crystal grains can be effectively suppressed from growing when the material that contains predetermined amounts of $SiO_2$, $TiO_2$ and MgO is fired at a relatively low temperature in a range from 1300 to 1500° C. so as to sinter, in the basic invention described above, wherein 65 to 96% by weight of $Al_2O_3$, 4 to 34.4% by weight of $ZrO_2$, 0.20% by weight or more $SiO_2$, 0.22% by weight or more $TiO_2$ and 0.12% by weight or more MgO are contained while the total amount of $SiO_2$, $TiO_2$ and MgO is in a range from 0.6 to 4.5% by weight.

According to the invention, the following conditions are preferably satisfied:
(1) Mean grain size of the $Al_2O_3$ is not larger than 3 µm and mean grain size of $ZrO_2$ is not larger than 0.5 µm;
(2) 20% or more of $ZrO_2$ content in the sintered ceramics forms crystal of tetragonal system;
(3) Atomic ratio Ti/Mg of $TiO_2$ and MgO is in a range from 0.5 to 1.2;
(4) At least a part of the $TiO_2$ and MgO is dissolved in $Al_2O_3$ crystal so as to form a solid solution crystal, and the total amount of these materials dissolved corresponds to 0.1% by weight or more of the $Al_2O_3$; and
(5) There are oxides of Ti and Mg or composite oxide grains that contain these oxides dispersed in at least part of the crystal grains of $Al_2O_3$.

The sintered ceramic described above can be consolidated at a low temperature while suppressing $Al_2O_3$ and $ZrO_2$ grains from growing during sintering, by containing predetermined amounts of $SiO_2$, $TiO_2$ and MgO as additives to $Al_2O_3$ and $ZrO_2$ of compositions in the ranges described above, thereby making it possible to form a high density structure consisting of fine particles and achieve high strength.

In the sintered material, it is preferable that mean grain size of $Al_2O_3$ is not larger than 3 µm and mean grain size of $ZrO_2$ is not larger than 0.5 µm. Also it is preferable that 20% or more of the total content of $ZrO_2$ in the sintered material forms crystal of tetragonal system.

By satisfying these conditions, phase transition enhancement effect can be effectively achieved. The atomic ratio (Ti/Mg) of $TiO_2$ and MgO in the additive is preferably in a range from 0.5 to 1.2. This enables it to suppress the formation of compounds that cause a decrease in strength, so as to obtain sintered material of higher strength.

It is preferable that at least a part of the $TiO_2$ and MgO is dissolved in an $Al_2O_3$ crystal thereby forming a solid solution crystal, and the total amount of these materials dissolved is 0.1% by weight or more of the $Al_2O_3$. This improves the strength of the $Al_2O_3$ crystal through the formation of the solid solution.

Moreover, it is also preferable that oxides of Ti or Mg or composite oxide grains are dispersed in at least part of the crystal grains of $Al_2O_3$.

Strength and toughness of the sintered ceramics can be improved further through the effect of dispersing the oxides of Ti or Mg or composite oxide grains.

According to the present invention, improvement in strength through a solid solution and improvement in strength through grain dispersion can be achieved in addition to making the structure finer, consolidation to high density and the phase transition enhancement in the $Al_2O_3$—$ZrO_2$ composite material, so as to obtain a biomedical member having high hardness, high strength and high wear resistance.

According to the present invention, it is preferable to include a process of sintering at a temperature in a range from 1300 to 1500° C. in oxidizing atmosphere and applying heat treatment to the sintered ceramics at a temperature at least 60° C. lower than the sintering temperature or further lower in a reducing atmosphere.

According to the present invention, it is particularly preferable to include a process of applying heat treatment to the sintered ceramics, that is obtained in the oxidizing atmosphere described above, at a temperature at least 60° C. lower than the sintering temperature or further lower in a reducing atmosphere. Sintering under these conditions makes it possible to change the degree of dissolution of oxides of Ti and Mg in $Al_2O_3$ and cause grains of compounds other than $Al_2O_3$ to precipitate in the $Al_2O_3$ crystal grains.

The biomedical member of the present invention that is formed from the sintered ceramics described above may be used as an artificial material that has affinity with living tissue without toxicity and does not cause rejection by the living tissue in applications such as artificial bone and artificial dental implant, where high strength is required as in the case of artificial head. The sintered ceramics is particularly excellent in ceramics-to-ceramics wear resistance in vivo environment, and the sintered ceramics can be used to make an artificial joint that has sliding interface between ceramic members.

Third invention is based on a finding that $Al_2O_3$ grains having shape anisotropy can be suppressed from being generated and suppress $ZrO_2$ grains that are dispersed from growing, by adding SrO to $Al_2O_3$—$ZrO_2$ composite material consisting of $Al_2O_3$ as the main component and sintering the material at a low temperature, and is characterized in that 65% by weight or more $Al_2O_3$, 4 to 34% by weight of $ZrO_2$ and 0.1 to 4% by weight of SrO are contained and Sr forms a solid solution with part of the $ZrO_2$ grains. According to the present invention, it is supposed that a small amount of Sr that normally does not form a solid solution can be caused to form a solid solution with $ZrO_2$ grains because $ZrO_2$ grains are surrounded by $Al_2O_3$ grains while strain is retained in the $ZrO_2$ grains, so that SrO serves as a stabilizing agent thereby improving strength and fracture toughness due to stress-induced phase transition into monoclinic system. Adding $TiO_2$, MgO and $SiO_2$ as the sintering additives further promotes the incorporation of Sr into a solid solution with $ZrO_2$ grains, thereby enhancing the effect of stress-induced phase transition. Therefore, according to the present invention, it is preferable that $TiO_2$, MgO and $SiO_2$ are contained as the sintering additives, while 0.20% by weight or more $SiO_2$, 0.22% by weight or more $TiO_2$ and 0.12% by weight or more MgO are contained and the total amount of $SiO_2$, $TiO_2$ and MgO is in a range from 0.6 to 4.5% by weight.

The present invention is characterized in that the main raw materials that contain Al, Zr and Sr in the form of metals or compounds are mixed so that the composite material that contains 65% by weight or more $Al_2O_3$, 4 to 34% by weight of $ZrO_2$ and 0.1 to 4% by weight of SrO, when contents of the metals or the compounds of the metals are converted to the contents of metal oxides, is formed into a predetermined shape and fired at a temperature in a range from 1300 to 1500° C. and is subjected to hot isostatic treatment at a temperature at least 30° C. lower than the sintering temperature.

In this case, it is preferable that the main raw materials that contain Al, Zr and Sr in the form of metals or compounds are provided with sintering additives that contains Ti, Mg and Si added thereto in the form of metals or compounds so that the composite material that contains 0.20% by weight or more $SiO_2$, 0.22% by weight or more $TiO_2$ and 0.12% by weight or more MgO, when contents of the metals or the compounds of the metals are converted to the contents of metal oxides, and the total amount of $SiO_2$, $TiO_2$ and MgO is in a range from 0.6 to 4.5% by weight.

According to the present invention, as the composite material has the composition in the range described above and Sr forms a solid solution with part of $ZrO_2$ grains, SrO exerts the effect of stabilizing tetragonal crystal of $ZrO_2$ thereby improving the strength and fracture toughness. Thus practically useful material is obtained that does not undergo an increase in the $ZrO_2$ content and decrease in strength due to the formation of $Al_2O_3$ grains having shape anisotropy.

While the biomedical member of the present invention is made by mixing the raw materials in predetermined amounts and forming the mixture into predetermined shape, the raw materials may also be in the form of powder, aqueous solution or other form of metals, oxides of the metals, hydroxides of the metals or salts such as metal carbonate. In case the raw material is used in the form of powder, the powder has a mean grain size preferably not larger than 1.0 µm. For the molding process, press molding, casting, cold isostatic molding, cold isostatic treatment or the like may be employed.

The present invention is also characterized in that the material is fired at a temperature in a range from 1300 to 1500° C. and is subjected to hot isostatic treatment at a temperature at least 30° C. lower than the sintering temperature. By this process, it is made possible to produce a consolidated material constituted from fine grains of $Al_2O_3$ and $ZrO_2$, in which $Al_2O_3$ grains having shape anisotropy is suppressed from being generated.

According to the present invention, significant effect of stress-induced phase transition is achieved in $ZrO_2$ where Sr forms a solid solution, and the effect is further enhanced by adding $TiO_2$, MgO and $SiO_2$ as the sintering additives. Addition of $SiO_2$, $TiO_2$ and MgO also decreases the sintering temperature, increases the density and makes the structure finer, thereby making it possible to provide the biomedical member made of material having high strength, high toughness and high hardness.

As will be made clear by the foregoing description, the $Al_2O_3$—$ZrO_2$ composite ceramics of the third invention becomes a material having high strength and high toughness due to the effect of stress-induced phase transition as the $ZrO_2$ grains with which Sr forms a solid solution constitute tetragonal system of quasi stabilized phase. This effect is further enhanced by adding $SiO_2$, $TiO_2$ and MgO as the sintering additives, and the sintering additives also make the sintering temperature lower, so that the sintered material is made denser and finer in structure without generating $Al_2O_3$ grains that have shape anisotropy. As a result, the biomedical member made of the composite material having high strength, high toughness and high hardness and an artificial joint formed therefrom can be provided.

Moreover, the composite ceramics has excellent sliding property without undergoing deterioration of surface properties caused by phase transition even in in vivo environment involving water in abundance. Thus the biomedical member of the present invention exhibits high wear resistance when used as a sliding member. Especially in the case of sliding motion between members both made of the composite material, specific wear can be restricted to within $0.3 \times 10^{-10}$ $mm^2/N$ after accelerated aging test conducted in saturated water vapor of 121° C. for 152 hours. Therefore, an artificial joint having sliding members that are made of the composite material and rub against each other achieves high strength, high toughness and high wear resistance.

DETAILED DESCRIPTION OF THE INVENTION

First Embodiment

Figure 1:
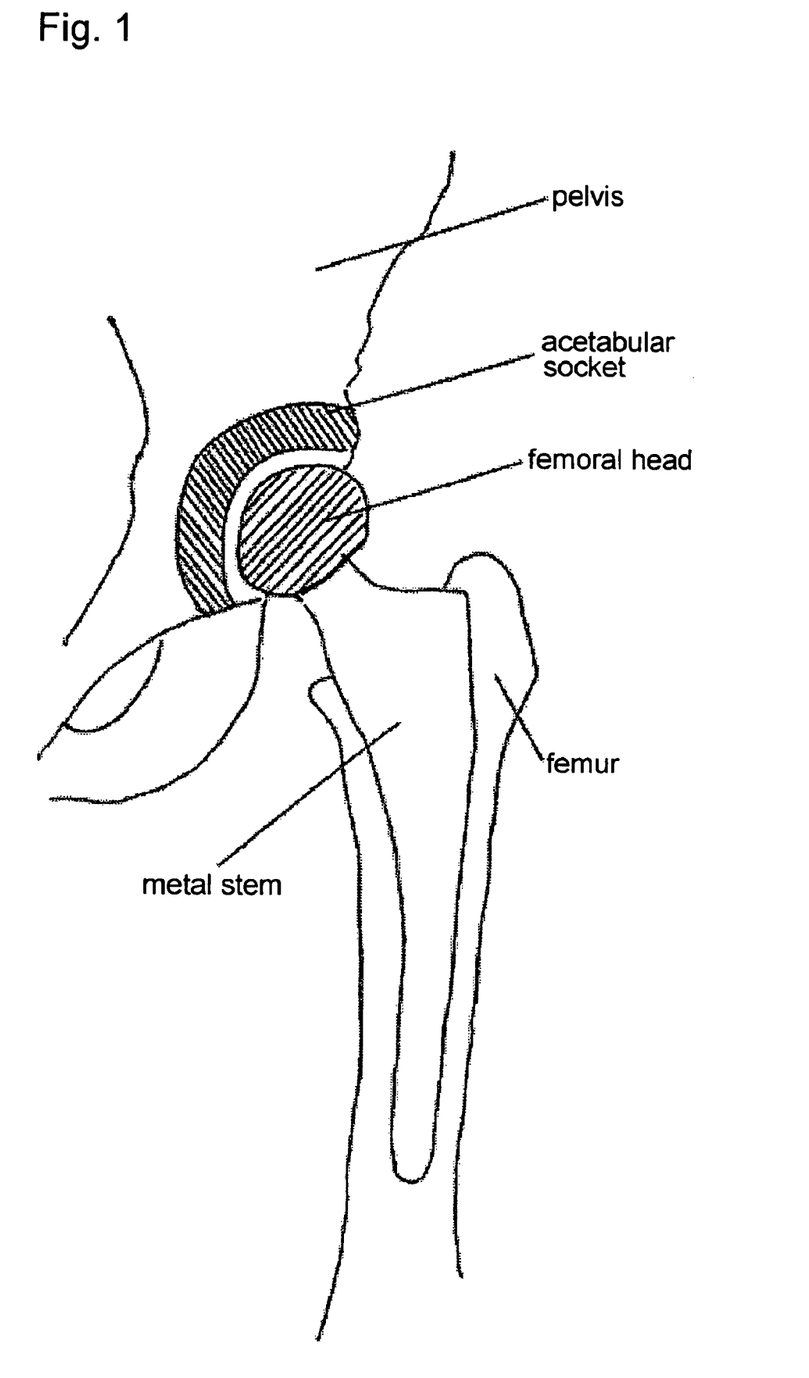
FIG. 1 schematically shows an artificial hip joint according to the first embodiment.
Figure 2:
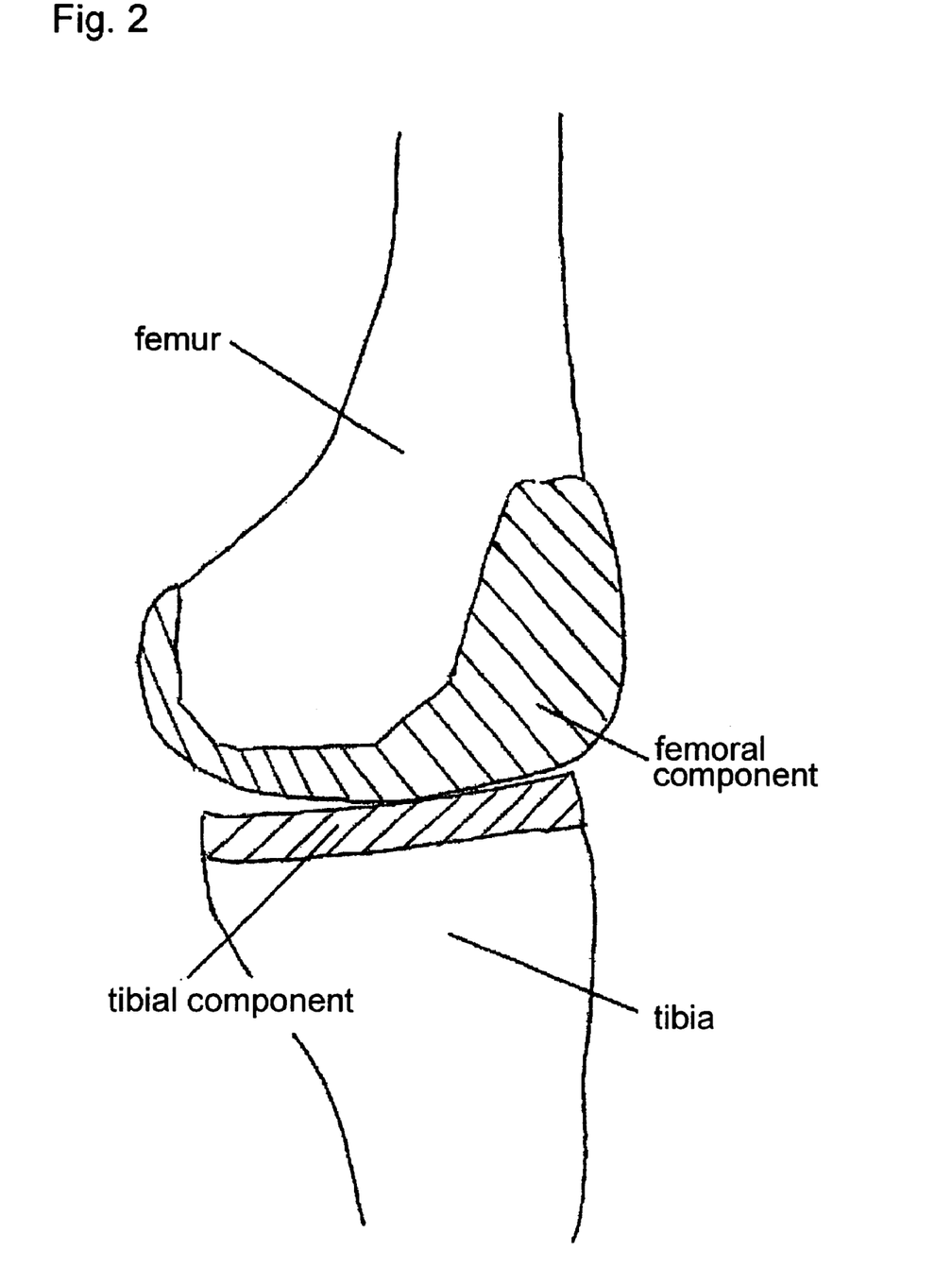
FIG. 2 schematically shows an artificial knee joint according to the first embodiment.

An embodiment of the biomedical member of the present invention is shown in FIG. 1 and FIG. 2. FIG. 1 shows an artificial joint that comprises sliding members formed from the composite ceramics. More particularly, an artificial hip joint is constituted from a metallic stem, a femoral head made of ceramics and an acetabulum socket. The present invention includes not only a case where mating sliding members of an artificial joint such as artificial hip joint are formed from the composite ceramics and a pair of biomedical members including the sliding members constitute an biomedical component (such as artificial joint), but also a case where only one of the sliding members is formed from the composite ceramics. FIG. 2 shows a femoral component of an artificial knee joint formed from the composite ceramics and a tibial component formed from ultra-high molecular polyethylene.

The biomedical member of the present invention also contains such a biomedical component that does not include sliding member. For example, an biomedical component, such as an artificial bone without joint is applicable.

Figure 3:
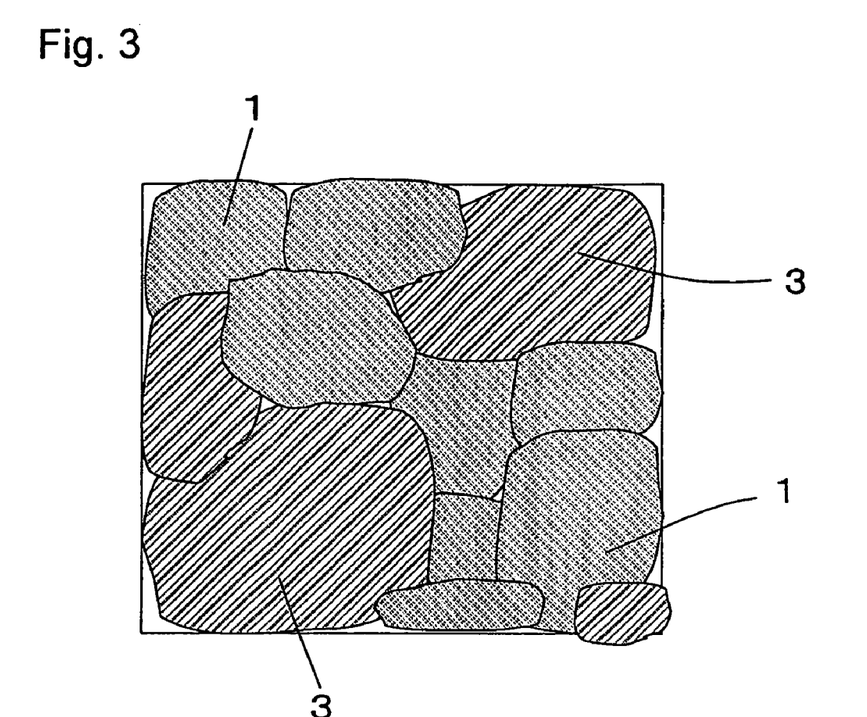
FIG. 3 schematically shows the inside of composite ceramics of the present invention.

FIG. 3 schematically shows the inside of the composite ceramics of the present invention. The composite ceramics of the present invention is constituted from zirconia crystal phase 1 that contains 2.8 to 4.5 mol % of $Y_2O_3$ and is partially stabilized and a metal phase 3 consisting of either Mo phase or W phase or both thereof. The content of $Y_2O_3$ contained in the zirconia crystal phase 1 is preferably in a range from 3 to 3.3 mol % for the purpose of stabilizing the tetragonal crystal of the zirconia crystal phase 1 or suppressing the generation of monoclinic crystal and cubic crystal. It is important that mean grain size of the zirconia crystal phase 1 is not larger than 0.35 µm, more preferably not larger than 0.25 µm. Lower limit of the mean grain size is preferably not less than 0.1 µm, more preferably not less than 0.15 µm. Forming grains of size smaller than the above requires it to use zirconia powder having a mean grain size smaller than this lower limit, which results in difficulty of molding the material.

The metal phase 3 preferably has mean grain size not larger than 1 µm, more preferably not larger than 0.8 µm for both Mo phase and W phase. Lower limit of the mean grain size is preferably not smaller than 0.4 µm.

It is important that the content of the metal phase 3 in the composite ceramics is in a range from 5 to 25% by weight, more preferably from 10 to 20% by weight. The metal phase 3 may contain at least one of Mo phase and W phase, while Mo phase is preferable.

According to the present invention, controlling the mean grain size of the zirconia crystal phase 1 to be smaller than that of the metal phase 3 makes it possible to decrease the likeliness of the metal phase 3 to be contained in the zirconia crystal phase 1. This means that grains of the zirconia crystal phase 1 do not grow so much as to contain the metal phase, such that the metal phase 3 is present only in the grain boundaries of the zirconia crystal phase 1. With this regards, mean grain size D1 of the zirconia crystal phase 1 and mean grain size D2 of the metal phase 3 preferably satisfy relationship of $0.3 \leq D1/D2 \leq 0.5$. The metal phase 3 contained in the composite ceramics of the present invention does not form a continuous phase that has elongated shape as in the case where higher The content of the metal phase 3 is contained, but the zirconia crystal phase 1 and the metal phase 3 exist in such a form as the grains of both phases are bonded with each other. In order to prevent the grains of the zirconia crystal phase 1 from growing, it is important that 95% or more, preferably 98% or more, of the metal phase 3 exists in the grain boundaries of the zirconia crystal phase 1.

When the concentration of $Y_2O_3$ contained in the zirconia crystal phase 1 that is the main component of the composite ceramics of the present invention is less than 2.8 mol %, initial mechanical property improves but monoclinic crystal that is quasi stable phase becomes more likely to precipitate (phase stability becomes lower), and therefore mechanical property after an autoclave treatment, for example, decreases to about half level. When the concentration of $Y_2O_3$ is higher than 4.5 mol %, on the other hand, the amount of cubic crystal phase increases.

In case a mean grain size of the zirconia crystal phase 1 is larger than 0.35 µm or a mean grain size of the metal phase 3 is larger than 1 µm, crystal grains grow while the metal phase 3 is contained in the zirconia crystal phase 1, and the volume of grain sloughed-off increases in sliding test such as wear resistance test, thus resulting in lower wear resistance.

Further in case the content of the metal phase 3 contained in the composite ceramics is less than 5% by weight, the effect of improving mechanical strength and toughness of the zirconia ceramics cannot be obtained. When the content is higher than 25% by weight, on the other hand, continuous phase of the metal phase 3 that has elongated shape is formed as described above. As a result, grains grow in increasing portion of the metal phase 3, thus making sloughed-off of the metal phase 3 more likely to occur in the wear resistance test thereby indicating lowering of the wear resistance.

In order to improve wear resistance by taking advantage of the high hardness of alumina phase, it is preferable that the composite ceramics of the present invention contains alumina phase in addition to the zirconia crystal phase and the metal phase. It is preferable that alumina phase also exists in the grain boundaries of the zirconia crystal phase. For this reason, mean grain size of the alumina phase is not larger than 0.5 µm, and more preferably not larger than 0.4 µm. Lower limit of the mean grain size is preferably not less than 0.1 µm, and more preferably not less than 0.15 µm. The content of the alumina phase is preferably not higher than 30% by weight, and more preferably in a range from 15 to 25% by weight.

Now a method for producing the composite ceramics of the present invention will be described.

The composite ceramics of the present invention is constituted from zirconia powder that contains 2.8 to 4.5 mol % of $Y_2O_3$ and either Mo powder or W powder or both thereof, and the mixed powder is formed into predetermined shape, with the compact being fired in a predetermined atmosphere so as to sinter.

In this case, it is important that mean grain size of the zirconia powder and the two kinds of metal powder is not larger than 0.3 µm and in a range from 0.3 to 1 µm, respectively. When the powder has mean grain size larger than these values, the zirconia crystal phase and the metal phase that constitute the sintered composite ceramics may have large mean grain size. Proper ranges of the mean grain size are from 0.15 to 0.25 µm for zirconia powder and 0.4 to 0.8 µm for metal powder.

The ceramic powder such as zirconia powder and the metal powder used in the present invention preferably have purity of 99.9% or higher.

The present invention is characterized in that the sintering process is carried out in two stages. First, preliminarily sintered material is prepared by sintering under atmospheric pressure. It is important that this sintering process is carried out in humidified atmosphere of nitrogen and hydrogen in mixture, in order to suppress the Mo powder and W powder from being oxidized, while at the same time suppressing the zirconia powder from being reduced.

It is important that the preliminarily sintered material thus prepared has relative density of 95% or higher, or more preferably 96% or higher in order to promote consolidation in the hot isostatic pressured sintering that is carried out subsequently.

The present invention is characterized in that the preliminarily sintered material is subjected to hot isostatic pressured sintering. In this sintering process, it is important that maximum temperature during the atmospheric pressure sintering and maximum temperature during the hot isostatic pressured sintering are both not higher than 1550° C. Restricting the maximum temperature during the sintering process to not higher than 1550° C. enables it to suppress the grains of the zirconia crystal phase and the metal phase from growing. Sintering temperature is preferably in a range from 1350 to 1550° C. for the atmospheric pressure sintering and in a range from 1250 to 1450° C. for the hot isostatic pressured sintering. The atmosphere for the hot isostatic pressured sintering is preferably argon gas atmosphere under a pressure of 1000 to 3000 atm.

The zirconia powder used in the present invention may be prepared either by calcinating a mixture of $Y_2O_3$ and zirconia powder, or by mixing metal salts of Y and zirconium and alkoxide in an aqueous solution of which pH value is controlled (hydrolysis method). Powder prepared by the hydrolysis method is preferably used since it has more uniform particle size and enables it to make more stable zirconia.

Alumina powder that is contained as the third phase in the composite ceramics of the present invention preferably has mean grain size of 0.6 µm or smaller, and more preferably 0.4 µm or smaller, while the lower limit of the mean grain size is preferably 0.1 µm or larger and more preferably 0.15 µm or larger.

According to the present invention, other ceramic powder may be added instead of, or in addition to, the alumina powder, as long as the wear resistance and other properties of the ceramics are not compromised.

Example 1

First, zirconia powder containing predetermined molar percentage of $Y_2O_3$ prepared by hydrolysis method and was partially stabilized (purity 99.9% and mean grain size 0.2 μm), Mo powder and W powder (both having purity of 99.9% or higher and mean grain size of 0.4 μm) and alumina powder (purity 99.9% and mean grain size 0.3 μm) were mixed in amounts shown in Table 1. The mixing process was carried out in a ball mill in wet process with IPA used as a solvent for a duration of 24 hours, by using alumina balls of high purity and high wear resistance and a polyethylene container. Then the mixed powder was dried and formed by press molding, with the compact being fired at 1400° C. in humidified atmosphere of nitrogen and hydrogen in mixture having the amount of $H_2/N_2=0.25$ and dew point of 30° C., thereby sintering the material and making rod-shaped preliminarily sintered material.

Of these sintered materials, those having relative density of 95% or higher were subjected to hot isostatic sintering under a pressure of 2000 atm with maximum temperature of 1350° C. thereby to make dense sintered material having relative density of 99.9% or higher. The sintered material thus made was ground to prepare samples measuring 4×3×35 mm.

The samples were tested to determine three-point bending strength at the room temperature per JIS-R1601 and fracture toughness by SEPB method per JIS-R1607. Identification and quantification of the crystal phase were carried out by X-ray diffraction. Crystal structure was observed under an Analytical Electron Microscope to determine the amounts of metal phase and zirconia phase. After accelerated aging test carried out in saturated water vapor of 121° C. for 152 hours, wear resistance was evaluated by means of pin-on-disk test method (JIS-T0303). Results of the tests are shown in Table 1.

The results shown in Table 1 show that samples Nos. 2 through 5, 8 through 11, 13, 14 and 16 that are composite ceramics within the scope of the present invention have three-point bending strength of 1320 MPa or higher, toughness of 5 or higher and specific amount of wear of 0.35 or less. Samples Nos. 2 through 5, 8 through 11, 13 and 14 that contain alumina phase having a mean grain size of 0.5 μm or smaller is contained as the third phase in the grain boundaries, in particular, have better properties with three-point bending strength being 1370 MPa or higher, toughness being 5.8 GPa or higher and specific amount of wear being 0.3 or less.

Samples out of the scope of present invention were inferior to the sample of the present invention in three-point bending strength, toughness and specific amount of wear.

Second Embodiment

The $Al_2O_3$—$ZrO_2$ composite material usually has higher value of Young's modulus and higher hardness as the content of $Al_2O_3$ becomes higher, but strength decreases due to the growth of crystal grains since the sintering temperature becomes higher. However, when the $Al_2O_3$—$ZrO_2$ composite material powder that contains $SiO_2$, $TiO_2$ and MgO powders added thereto is fired, eutectic point of the material decreases to 1300° C. or lower, so that sintering of the material is significantly accelerated and sintered material of higher density can be obtained while maintaining fine structure even at a temperature lower than the temperature employed in the prior art.

The high strength described above is more effectively achieved when the material has such a composition as high value of Young's modulus and high hardness can be obtained that contain 65% by weight or more $Al_2O_3$.

Accordingly, the sintered ceramics of the present invention contains 65% by weight or more, preferably 70% by weight or more $Al_2O_3$. The content of $Al_2O_3$ is 96% by weight or less, preferably 90% by weight or less and more preferably 85% by weight or less. By setting the content of $Al_2O_3$ in the range from 65 to 96% by weight, high strength and high hardness can be achieved.

The content of $ZrO_2$ is 4% by weight or more, preferably 10% by weight or more and more preferably 15% by weight or more. The content of $ZrO_2$ is 34.4% by weight or less, preferably 30% by weight or less and more preferably 25% by weight or less. By setting the content of $ZrO_2$ in the range from 4 to 34.4% by weight, reduction of grain size can be achieved.

In order to keep the eutectic point to 1300° C. or lower when sintering the materials of $Al_2O_3$ and $ZrO_2$ with $SiO_2$, $TiO_2$ and MgO added thereto, the content of $SiO_2$ is 0.20% by

TABLE 1

| Sample No. | Zirconia $Y_2O_3$ Molar % | crystal phase Mean grain size μm | Mo % by weight | Metal phase W % by weight | Mean grain size μm | Amount of metal phase in grain boundaries % | Alumina % by weight | Three-point bending strength MPa | Toughness GPa | Specific wear $mm^2/N$ $(\times 10^{-10})$ |
|---|---|---|---|---|---|---|---|---|---|---|
| *1 | 2.5 | 0.25 | 15 | 0 | 0.8 | 95 | 20 | 1720 | 6.5 | 1.24 |
| 2 | 2.8 | 0.25 | 15 | 0 | 0.8 | 95 | 20 | 1630 | 6.2 | 0.11 |
| 3 | 3 | 0.25 | 15 | 0 | 0.8 | 95 | 20 | 1600 | 6.1 | 0.08 |
| 4 | 4 | 0.25 | 15 | 0 | 0.8 | 95 | 20 | 1440 | 6 | 0.14 |
| 5 | 4.5 | 0.25 | 15 | 0 | 0.8 | 95 | 20 | 1370 | 5.8 | 0.27 |
| *6 | 5 | 0.25 | 15 | 0 | 0.8 | 95 | 20 | 1100 | 4.2 | 3.34 |
| *7 | 3 | 0.25 | 3 | 0 | 0.8 | 95 | 20 | 1150 | 4.5 | 0.12 |
| 8 | 3 | 0.25 | 10 | 0 | 0.8 | 95 | 20 | 1490 | 5.6 | 0.14 |
| 9 | 3 | 0.25 | 15 | 0 | 0.8 | 95 | 20 | 1590 | 6 | 0.23 |
| 10 | 3 | 0.25 | 20 | 0 | 0.8 | 95 | 20 | 1680 | 6.4 | 0.28 |
| 11 | 3 | 0.25 | 25 | 0 | 0.8 | 95 | 20 | 1740 | 6.7 | 0.30 |
| *12 | 3 | 0.25 | 30 | 0 | 0.8 | 95 | 20 | Unable to evaluate due to sintering failure | | |
| 13 | 3 | 0.25 | 0 | 15 | 0.8 | 95 | 20 | 1520 | 5.8 | 0.18 |
| 14 | 3 | 0.25 | 10 | 10 | 0.8 | 95 | 20 | 1570 | 6.2 | 0.25 |
| *15 | 3 | 0.4 | 15 | 0 | 0.3 | 70 | 20 | 1190 | 6.2 | 1.77 |
| 16 | 3 | 0.25 | 15 | 0 | 0.8 | 95 | 0 | 1320 | 5 | 0.35 |

* Samples out of the scope of present invention.

weight or more and preferably 0.4% by weight or more, the content of $TiO_2$ is 0.22% by weight or more and preferably 0.3% by weight or more, and the content of MgO is 0.12% by weight or more and preferably 0.2% by weight or more.

When the contents of $SiO_2$, $TiO_2$ and MgO are less than 0.20% by weight, less than 0.22% by weight and less than 0.12% by weight, respectively, liquid phase formed at the sintering temperature has higher viscosity which leads to less effect of accelerating the sintering reaction.

The total content of $SiO_2$, $TiO_2$ and MgO is in a range from 0.6 to 4.5% by weight, and preferably from 1.0 to 3.0% by weight. By controlling the total content in this range, the consolidation effect and the effect of forming structure of finer grains can be achieved.

Hardness of the sintered ceramics of the present invention can be improved by substituting a part of $Al_2O_3$ in the composition described above with $Cr_2O_3$ so as to form a solid solution, or substituting a part of $ZrO_2$ with $HfO_2$ so as to form a solid solution. Other compounds may also be added for the purpose of suppressing the crystal grains from growing or promoting shape-anisotropic growth of the crystal.

Now preferred forms of the sintered ceramics of the present invention will be described.

(1) In order to obtain sintered ceramics having high strength, mean grain size of $Al_2O_3$ contained in the sintered material is preferably 3 μm or smaller and more preferably 2 μm or smaller, and mean grain size of $ZrO_2$ in the sintered material is preferably 0.5 μm or smaller and more preferably 0.3 μm or smaller. By controlling the mean grain size in this way, it is made possible to not only improve the strength through the reduction of grain size but also increase the phase transition enhancement effect through uniform dispersion of finer $ZrO_2$ grains.

(2) In the sintered ceramics of the present invention, it is preferable that 20% or more, and preferably 40% or more of the $ZrO_2$ grains are formed in tetragonal system. It is possible to have tetragonal system in quasi stable state at the room temperature by adding various stabilizing agents such as Y, Ce, Mg or Ca to $ZrO_2$. In case a small amount of such stabilizing agent is added, for example when 2 mol % or less $Y_2O_3$ is added to $ZrO_2$, phase transition to monoclinic crystal is suppressed through the reduction of grain size, potential for phase transition to take place under stress becomes higher and phase transition enhancement effect is improved.

(3) Atomic ratio (Ti/Mg) of $TiO_2$ and MgO contents in the sintered ceramics of the present invention is preferably in a range from 0.5 to 1.2, within the range of compositions described above. When the atomic ratio (Ti/Mg) is 0.5 or higher, viscosity of the liquid phase can be effectively prevented from increasing at the sintering temperature, thus achieving better effect of accelerating the sintering reaction. When the atomic ratio (Ti/Mg) is 1.2 or lower, $Al_2TiO_5$ phase that has significant anisotropy in thermal expansion coefficient can be suppressed from being generated through the reaction of $TiO_2$ and $Al_2O_3$, thereby preventing the strength from decreasing. In order to make the material easier to sinter and suppress the generation of $Al_2TiO_5$ phase, the atomic ratio (Ti/Mg) is more preferably in a range from 0.7 to 1.0.

When the atomic ratio (Ti/Mg) is within the range described above, an effect of forming a solid solution effectively by means of $Al_2O_3$ crystal can also be obtained.

(4) One of preferable forms of the sintered ceramics of the present invention is such that $TiO_2$ and MgO are dissolved in $Al_2O_3$ to form a solid solution crystal so as to decrease the grain boundaries phase in the sintered material and increase the hardness while making $Al_2O_3$ crystal stronger thereby to increase the strength of the material. In case only a small amount of $TiO_2$ and MgO is dissolved in $Al_2O_3$ crystal, the effect described above diminishes. Therefore, the amount of $TiO_2$ and MgO dissolved in $Al_2O_3$ is preferably 0.1% by weight or more relative to the quantity of $Al_2O_3$. In this case, it is more preferable that the amount of $TiO_2$ and MgO dissolved in $Al_2O_3$ is 0.5% by weight or more relative to the quantity of $Al_2O_3$.

(5) Another preferable aspect of the present invention is the dispersion of oxides of Ti and Mg or composite oxide grains that contain them in at least a part of the $Al_2O_3$ crystal grains. The solid solution formed through dissolution of oxides of Ti and Mg or composite oxide that contain these oxides into the $Al_2O_3$ crystal precipitates, under the condition of less amount of dissolution, thus forming a structure where fine grains of $TiO_2$ and $MgAl_2O_4$ are dispersed in the $Al_2O_3$ crystal grains. This greatly improves the strength of the material due to the effect of dispersing fine grains. Size of the fine grains along the major axis is preferably 0.2 μm or smaller, and more preferably 0.1 μm or smaller.

The sintered ceramics of the present invention can be produced by using various known ceramics. The sintered ceramics of the present invention is produced first by mixing the raw materials in predetermined amounts and the mixture is formed into a predetermined shape. The raw materials may be in the form of powder, aqueous solution or other form of oxides, metals, carbonates of the metals or salts such as hydroxides of the metals.

In case the raw material is used in the form of powder, the powder has mean grain size preferably not larger than 1.0 μm.

For the molding process, press molding, casting, cold isostatic molding, cold isostatic treatment or the like may be employed. According to the present invention, it is important to fire at a temperature in a range from 1300 to 1500° C. When the sintering temperature is lower than 1300° C., dense sintered material cannot be obtained. When the sintering temperature is higher than 1500° C., crystal grains grow. In either case, it is difficult to obtain sintered material having high strength. Based on the foregoing discussion, it is desirable to fire the material at a temperature in a range from 1350 to 1450° C. Also according to the present invention, after the sintering process described above, it is desirable that the material thus fired is subjected to hot isostatic sintering at a temperature at least 60° C. lower than the sintering temperature (from 1350 to 1450° C.). In addition, after the hot isostatic sintering, it is preferable to carry out heat treatment in a reducing atmosphere at a temperature at least 60° C. lower than the sintering temperature (from 1350 to 1450° C.).

In case the sintering process described above is carried out in an oxidizing atmosphere such as air or mixed gas atmosphere that contains oxygen with a certain level of partial pressure of oxygen, $TiO_2$ and Mg dissolve into $Al_2O_3$ crystal grains.

According to the present invention, as the sintered material thus obtained is subjected to heat treatment in a reducing atmosphere at a temperature at least 60° C. lower than the sintering temperature, particularly from 1100 to 1350° C., number of valence of Ti changes from 4 to 3 thereby increasing the solubility of $TiO_2$. As a result, since the solubility of Mg decreases, a composite comprising Mg contained in $Al_2O_3$ crystal grain, namely $MgAl_2O_4$, precipitates. This results in the sintered ceramics of the present invention that is enhanced with the fine grains dispersed therein.

Example 2

$Al_2O_3$ powder having purity of 99.9% and mean crystal grain size of 0.5 μm, $ZrO_2$ powder having purity of 99.9% and mean grain size of 0.2 μm, quasi stabilized $ZrO_2$ containing 0, 1.5, 2 and 3 mol % of $Y_2O_3$, $SiO_2$, $TiO_2$ and $Mg(OH)_2$ powders having purity of 99.9% or higher and mean grain sizes in a range from 0.5 to 1.0 μm were mixed in amounts shown in Table 2 in isopropyl alcohol used as a solvent. The mixture was molded under a pressure of 100 MPa, followed by cold isostatic treatment under a pressure of 300 MPa. The compact was then fired in air atmosphere at the temperature shown in Table 1 for 5 hours. Some of the samples were further subjected to hot isostatic treatment under a pressure of 200 MPa in an atmosphere of Ar—$O_2$ gas mixture ($O_2$ concentration being 20% by volume) at the temperature shown in Table 1 (HIP temperature). Furthermore, some of the samples were subjected to heat treatment in hydrogen atmosphere at the temperature (hydrogen treatment temperature) shown in Table 1 for 5 hours.

Crystal grain sizes of $Al_2O_3$ and $ZrO_2$ were measured on a micrograph of a fracture surface of the sintered material taken by means of a Scanning Electron Microscope.

The amount of tetragonal $ZrO_2$ crystal in the total $ZrO_2$ was determined from X-ray diffraction intensity, using the following equation.

The amount of tetragonal crystal (%)=$It/(Im1+Im2+It)$

Where It: Intensity of X-ray diffraction from (111) plane of tetragonal system

Im1: Intensity of X-ray diffraction from (111) plane of monoclinic system

Im2: Intensity of X-ray diffraction from (−11−1) plane of monoclinic system

Quantities of $TiO_2$ and MgO that were dissolved were estimated by measuring the lattice constant of $Al_2O_3$ for some of the samples. Samples subjected to heat treatment in hydrogen atmosphere were observed under a Transmission Electron Microscope and it was confirmed that fine grains of $MgAl_2O_4$ were precipitated and dispersed in the crystal grains.

The samples were subjected to three-point bending test and Vickers hardness test, with the results shown in Table 3 along with the results of the micro-structural analysis.

TABLE 2

| No. | $Al_2O_3$ % by weight | $ZrO_2$ % by weight | $Y_2O_3$ concentration in $ZrO_2$ mol % | Additive % by weight of $SiO_2$ | % by weight of $TiO_2$ | % by weight of MgO | Total content, % by weight | Sintering temperature ° C. | HIP temperature ° C. | Hydrogen treatment temperature ° C. |
|---|---|---|---|---|---|---|---|---|---|---|
| 1 | 65 | 33 | 2 | 0.5 | 1 | 0.5 | 2 | 1300 | — | — |
| 2 | 71 | 27 | 2 | 0.5 | 1 | 0.5 | 2 | 1350 | — | — |
| 3 | 78 | 20 | 2 | 0.5 | 1 | 0.5 | 2 | 1350 | — | — |
| 4 | 90 | 8 | 2 | 0.5 | 1 | 0.5 | 2 | 1400 | — | — |
| 5 | 93 | 5 | 2 | 0.5 | 1 | 0.5 | 2 | 1450 | — | — |
| * 6 | 80 | 20 | 1.5 | 0 | 0 | 0 | 0 | 1570 | — | — |
| * 7 | 79.5 | 20 | 1.5 | 0.2 | 0.2 | 0.1 | 0.5 | 1550 | — | — |
| * 8 | 78.5 | 20 | 1.5 | 0.1 | 0.9 | 0.5 | 1.5 | 1510 | — | — |
| 9 | 79.2 | 20 | 1.5 | 0.4 | 0.25 | 0.15 | 0.8 | 1400 | — | — |
| 10 | 78.6 | 20 | 1.5 | 0.5 | 0.6 | 0.3 | 1.4 | 1400 | — | — |
| 11 | 77.5 | 20 | 1.5 | 1 | 1 | 0.5 | 2.5 | 1350 | — | — |
| 12 | 75.8 | 20 | 1.5 | 1.8 | 1.6 | 0.8 | 4.2 | 1300 | — | — |
| * 13 | 75 | 20 | 1.5 | 2 | 2 | 1 | 5 | 1300 | — | — |
| 14 | 83.6 | 15 | — | 0.8 | 0.3 | 0.3 | 1.4 | 1300 | 1200 | — |
| 15 | 83.2 | 15 | — | 0.8 | 0.6 | 0.4 | 1.8 | 1350 | 1250 | — |
| 16 | 83 | 15 | — | 0.8 | 0.8 | 0.4 | 2 | 1350 | 1250 | — |
| 17 | 83.2 | 15 | — | 0.8 | 0.7 | 0.3 | 1.8 | 1350 | 1250 | — |
| 18 | 83.1 | 15 | — | 0.8 | 0.8 | 0.3 | 1.9 | 1350 | 1250 | — |
| 19 | 78 | 20 | 3 | 0.5 | 1 | 0.5 | 2 | 1350 | 1250 | — |
| 20 | 78 | 20 | 3 | 0.5 | 1 | 0.5 | 2 | 1350 | 1250 | 1200 |
| 21 | 78 | 20 | 2 | 0.5 | 1 | 0.5 | 2 | 1350 | 1250 | 1250 |
| 22 | 78 | 20 | 1.5 | 0.5 | 1 | 0.5 | 2 | 1350 | 1250 | 1250 |
| 23 | 78 | 20 | — | 0.5 | 1 | 0.5 | 2 | 1350 | 1250 | 1250 |

TABLE 3

| No. | Mean grain size μm $Al_2O_3$ | Mean grain size μm $ZrO_2$ | Tetragonal $ZrO_2$ % | Dissolution of $TiO_2$ and MgO in $Al_2O_3$ Atomic % | Precipitated grains in $Al_2O_3$ crystal grains | Breakage strength MPa | Hardness Hv |
|---|---|---|---|---|---|---|---|
| 1 | 0.8 | 0.2 | 92 | 0.4 | — | 1720 | 1705 |
| 2 | 0.8 | 0.2 | 97 | 0.55 | — | 1711 | 1712 |
| 3 | 1.1 | 0.2 | 88 | 0.55 | — | 1545 | 1794 |
| 4 | 1.5 | 0.3 | 91 | 0.85 | — | 1320 | 1810 |
| 5 | 1.8 | 0.4 | 96 | 0.9 | — | 1308 | 1846 |
| * 6 | 3.8 | 1.2 | 38 | 0 | — | 1129 | 1643 |
| * 7 | 3.5 | 0.7 | 45 | 0.2 | — | 1081 | 1630 |
| * 8 | 3.1 | 0.6 | 67 | 1.1 | — | 1142 | 1635 |
| 9 | 2.2 | 0.5 | 78 | 0.23 | — | 1421 | 1811 |
| 10 | 2.4 | 0.5 | 79 | 0.4 | — | 1576 | 1790 |
| 11 | 1.6 | 0.5 | 73 | 0.5 | — | 1467 | 1775 |
| 12 | 1.3 | 0.4 | 76 | 0.4 | — | 1623 | 1764 |
| * 13 | 3.2 | 0.8 | 43 | 0.4 | — | 1092 | 1590 |
| 14 | 1.2 | 0.3 | 85 | 0.3 | — | 1742 | 1823 |
| 15 | 1.3 | 0.3 | 87 | 0.5 | — | 1651 | 1771 |
| 16 | 1.3 | 0.3 | 83 | 0.6 | — | 1587 | 1750 |
| 17 | 1.3 | 0.3 | 91 | 0.5 | — | 1505 | 1734 |
| 18 | 1.3 | 0.3 | 88 | 0.5 | — | 1474 | 1713 |

TABLE 3-continued

| No. | Mean grain size μm Al$_2$O$_3$ | Mean grain size μm ZrO$_2$ | Tetragonal ZrO$_2$ % | Dissolution of TiO$_2$ and MgO in Al$_2$O$_3$ Atomic % | Precipitated grains in Al$_2$O$_3$ crystal grains | Breakage strength MPa | Hardness Hv |
|---|---|---|---|---|---|---|---|
| 19 | 1.5 | 0.3 | 84 | 0.6 | — | 1562 | 1769 |
| 20 | 1.5 | 0.3 | 89 | 0.6 | MgAl$_2$O$_4$ | 1741 | 1827 |
| 21 | 1.5 | 0.3 | 92 | 0.3 | MgAl$_2$O$_4$ | 1773 | 1838 |
| 22 | 1.5 | 0.3 | 84 | 0.3 | MgAl$_2$O$_4$ | 1726 | 1824 |
| 23 | 1.4 | 0.3 | 83 | 0.3 | MgAl$_2$O$_4$ | 1813 | 1859 |

As will be apparent from Table 2 and Table 3, the sintered ceramics according to the present invention showed breakage strength of 1300 MPa or higher, high strength and high hardness of 1700 Hv or higher in terms of Vickers hardness. Samples Nos. 20 through 23, in particular, showed excellent properties such as breakage strength of 1700 MPa or higher and high hardness of 1800 Hv or higher in terms of Vickers hardness, by combining the effect of strengthening by dispersed fine grains.

Sample No. 6 did not contain SiO$_2$, TiO$_2$ and MgO, sample No. 7 contained less quantities of these additives than the sample of the present invention, and sample No. 8 contained less The content of SiO$_2$. As a result, sintering temperature was higher for all of these samples which showed lower strength and lower hardness due to the growth of crystal grains. Sample No. 13 contained excessive quantities of the additives and therefore showed lower strength and lower hardness due to the formation of much grain boundaries phase.

Example 3

Test pieces prepared from the materials of Nos. 6, 16 and 21 shown in Table 2 were subjected to accelerated aging test conducted at 121° C. for 152 hours, and were then subjected to pin-on-disk test specified in JIS-T0303 to evaluate the wear resistance. Results of the tests are shown in Table 4.

TABLE 4

| Sample No. | Surface roughness Ra nm Before test | Surface roughness Ra nm After test | Specific wear mm$^2$/N (×10$^{-10}$) |
|---|---|---|---|
| *6 | 2.1 | 5.2 | 2.78 |
| 16 | 1.8 | 2.1 | 0.27 |
| 21 | 1.7 | 1.9 | 0.22 |

It can be seen that samples Nos. 16 and 21 of the present invention underwent less wear and showed better surface conditions after wearing, than sample No. 6 that was out of the scope of the present invention.

Third Embodiment

Figure 4:
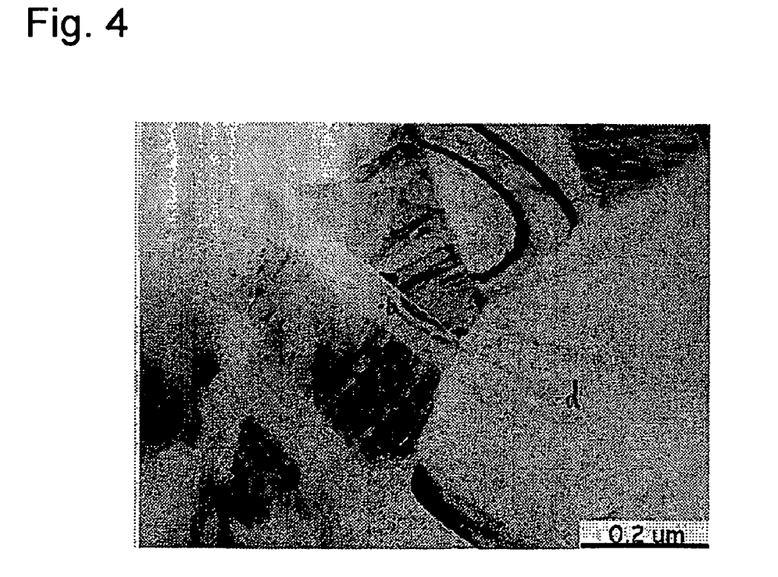
FIG. 4 is a TEM micrograph showing the structure of sample No. 1.

An embodiment of the biomedical member of the present invention is shown in FIG. 1 and FIG. 2. FIG. 4 shows an artificial joint that comprises sliding members formed from the composite material. More particularly, an artificial hip joint is constituted from a metallic stem, a femoral head made of ceramics and an acetabulum socket. The present invention contains not only a case where mating sliding members of an artificial joint such as artificial hip joint are formed from the composite material and a pair of biomedical members including the sliding members constitute the artificial joint, but also a case where only one of the sliding members is formed from the composite material. FIG. 5 shows a femoral component of an artificial knee joint formed from the composite material and a tibial component formed from ultra high molecular polyethylene.

The biomedical member of the present invention also contains such an biomedical component that does not include sliding member, such as an artificial bone without joint.

Mechanical property of ZrO$_2$ can be improved by causing proper amount of stabilizing agent such as Y$_2$O$_3$ to form a solid solution with ZrO$_2$. However, addition of excessive amount of Y$_2$O$_3$ to the Al$_2$O$_3$—ZrO$_2$ composite ceramics causes cubic crystal phase to increase, thus diminishing the contribution of phase transition to the fracture toughness. When the addition of Y$_2$O$_3$ is insufficient, on the other hand, the amount of monoclinic ZrO$_2$ increases and both strength and toughness become lower. Increasing the content of Al$_2$O$_3$ leads to an increase in hardness, but strength and toughness become lower.

In order to compensate for the adverse effects described above, SrO is added so as to improve the fracture toughness through the formation of grains having shape anisotropy, but this requires it to fire at a higher temperature which results in significant decrease in strength and in hardness due to the growth of grains and impediment to compaction.

In the case of the material developed according to the present invention, while tetragonal crystal of ZrO$_2$ is stabilized by the formation of a solid solution of Sr, although cubic crystal is less likely to be formed since smaller amount of Sr forms a solid solution with ZrO$_2$. As a result, the effect of stress-induced phase transition is achieved significantly so that fracture toughness can be improved without forming grains that have shape anisotropy, thus improving both strength and hardness.

The composite material that constitutes the biomedical member of the present invention contains at least Al$_2$O$_3$, ZrO$_2$ and SrO, and is characterized in that 65% by weight or more Al$_2$O$_3$, 4 to 34% by weight of ZrO$_2$ and 0.1 to 4% by weight of SrO are contained and Sr forms a solid solution with a part of the ZrO$_2$ grains. It is preferable that the content of Al$_2$O$_3$ is 65% by weight or more, preferably from 67 to 90% by weight, and more preferably from 76 to 84% by weight, and the content of ZrO$_2$ is from 4 to 34% by weight, preferably from 10 to 34% by weight, and more preferably from 11 to 20% by weight.

Composition containing 65% by weight or more Al$_2$O$_3$ achieves high strength and high hardness. When the content of ZrO$_2$ is less than 4% by weight, strength and toughness become low. When the content of ZrO$_2$ exceeds 34% by weight, value of Young's modulus decreases thus resulting in low hardness.

The content of SrO added to the composite material is from 0.1 to 4% by weight, preferably from 0.5 to 3% by weight, and more preferably from 0.7 to 1.5% by weight.

It is important to control the added quantity of SrO within a range from 0.1 to 4% by weight.

When the added quantity of SrO is less than 0.1% by weight, much monoclinic crystal of $ZrO_2$ is formed which results in lower strength. When the added quantity of SrO exceeds 4% by weight, sintering temperature becomes higher, thus resulting in impediment to compaction due to the formation of $Al_2O_3$ grains having shape anisotropy and decrease in strength and in hardness due to the growth of $ZrO_2$ grains.

Adding predetermined amounts of $SiO_2$, $TiO_2$ and MgO to the composition in the range described above makes it possible to consolidate the sintered material at a lower temperature while suppressing the $Al_2O_3$ and $ZrO_2$ crystal grains from growing, thereby achieving higher strength through the formation of structure consisting of fine grains with high density.

High strength, high toughness and high hardness can be achieved when 65% by weight or more $Al_2O_3$, 4 to 34% by weight of $ZrO_2$, from 0.1 to 4% by weight of SrO, 0.20% by weight or more $SiO_2$, 0.22% by weight or more $TiO_2$ and 0.12% by weight or more MgO are contained, and the total amount of $SiO_2$, $TiO_2$ and MgO is in a range from 0.6 to 4.5% by weight.

The composition contains 0.20% by weight or more, preferably from 0.4 to 1.5% by weight of $SiO_2$, and 0.22% by weight or more, preferably from 0.3 to 0.7% by weight of $TiO_2$ and 0.12% by weight or more, preferably from 0.2 to 1.4% by weight of MgO.

When the content of $SiO_2$ is less than 0.20% by weight, or the content of $TiO_2$ is less than 0.22% by weight, or the content of MgO is less than 0.12% by weight, there occurs not enough formation of liquid phase and it becomes difficult for $Al_2O_3$ to compact.

Adding $SiO_2$, $TiO_2$ and MgO in the amounts described above as the sintering additives promotes the incorporation of Sr into a solid solution with $ZrO_2$ grains so as to improve the strength and toughness while decreasing the eutectic point to 1300° C. or lower, and results in the formation of liquid phase during the sintering process, thus significantly promoting the sintering reaction of the material. As a result, sintered material of high density can be obtained even at a low temperature. As the material is sintered at a relatively low temperature, $Al_2O_3$ grains having shape anisotropy are suppressed from growing so that fine structure is obtained and the strength and the hardness do not decrease.

In order to obtain a material having high strength, high toughness and high hardness, it is important to suppress the $Al_2O_3$ and $ZrO_2$ grains from growing by sintering at a low temperature of 1500° C. or lower, preferably 1490° C. or lower. When fired at a high temperature with SrO added, $Al_2O_3$ grains having shape anisotropy will grow thus causing strength, toughness and hardness to decrease. This is because the growth of $ZrO_2$ grains leads to increasing the amount of monoclinic $ZrO_2$ that causes strength and hardness to decrease.

The $Al_2O_3$—$ZrO_2$ composite ceramics of the present invention having the composition described above avoids such problems as impediment against compaction by the $Al_2O_3$ grains that have shape anisotropy and decrease in strength or hardness due to the growth of $ZrO_2$ grains. For example, it is preferable that $Al_2O_3$ grains in the composite ceramics have elongated shape in SEM image, mean value of largest dimensions of the $Al_2O_3$ grains, namely the size along the major axis thereof, is 1.5 μm or less, ratio of the major axis size to the smallest dimension of the $Al_2O_3$ grain, namely the size along minor axis that is perpendicular to the major axis, referred to as the aspect ratio, is 2.5 or less and median value between the mean minor axis size and the mean major axis size is 1 μm or less. When the mean aspect ratio of the $Al_2O_3$ grains is larger than 2.5 or the mean major axis size is larger than 1.5 μm, compaction is impeded by the grains having shape anisotropy thus resulting in low strength. In case the median value of the $ZrO_2$ grains between the mean minor axis size and mean major axis size is larger than 1.0 μm, stability of the tetragonal crystal decreases and cracks occur due to phase transition, thus resulting in decrease in strength and in toughness.

Thus it is important that the material is fired at a temperature of 1500° C. or lower and is consolidated by hot isostatic sintering while suppressing the $Al_2O_3$ and $ZrO_2$ grains from growing. The hot isostatic sintering is carried out at a temperature at least 30° C., preferably at least 50° C., and more preferably at least 100° C. lower than the temperature of the main sintering process.

Example 4

$Al_2O_3$ powder having purity of 99.95% and mean particle size of 0.22 μm, $ZrO_2$ powder having purity of 99.95% and mean particle size of 0.4 μm, $Mg(OH)_2$ powder having mean particle size of 0.6 μm, $SiO_2$ powder having mean particle size of 0.5 μm and SrO powder having mean particle size of 0.2 μm were mixed in amounts shown in Table 1. The mixed powder was molded under a pressure of 1 ton/cm$^2$, followed by hydrostatic treatment under a pressure of 3 ton/cm$^2$ thereby making a compact. The compact was subjected to main sintering and Hot Isostatic Sintering (indicated as HIP in Table) at the temperatures shown in Table 2.

Sintered materials thus obtained were subjected to breakage strength test at the room temperature per JIS-R1601, fracture toughness test by SEPB method per JIS-R1607 and Vickers hardness test per JIS R1610. Crystal grain size was measured as follows. Test piece was polished to mirror finish and was subjected to thermal etching at a temperature about 50° C. lower than the sintering temperature. The polished surface was photographed using SEM in such a manner that the image contains 100 $Al_2O_3$ grains and 100 $ZrO_2$ grains. $Al_2O_3$ crystal grains that were captured in complete grain shape in the micrograph were picked up, and the largest dimension along the major axis and the largest dimension along the minor axis that is perpendicular to the major axis were measured on these grains so as to calculate the aspect ratio.

After accelerated aging test conducted in saturated water vapor of 121° C. for 152 hours, wear resistance was evaluated by pin-on-disk test method (JIS T0303, however the test pieces were formed from the composite material). Results of the test are shown in Table 2. It was confirmed by X-ray diffraction (XRD) analysis that tetragonal $ZrO_2$ crystal was stabilized by SrO. It was also confirmed by means of an Electron Probe Microanalyzer (EPMA) that Sr formed a solid solution with $ZrO_2$.

From Table 2, it can be seen that the material (sample No. 8) that contained SrO but did not contain other sintering additives showed higher strength and higher fracture toughness than the material (sample No. 12) that did not contain SrO. The materials (samples Nos. 1, 2, 6 and 14) that contained SrO and the sintering additives $SiO_2$, $TiO_2$ and MgO and were sintered at a lower temperature showed better characteristics than those of the sample No. 8, with strength in a range from 1410 to 1540 MPa, fracture toughness in a range from 5.1 to 5.4 MPa√m and hardness in a range from 1740 to 1790 Hv.

The material of sample No. 4 showed higher sintering temperature and contained a small amount of grains having shape anisotropy generated therein. As a result, this sample showed strength and hardness that were a little lower, but showed fracture toughness higher than that of sample No. 8. In the material (sample No. 12) that contained $ZrO_2$ where $Y_2O_3$ formed a solid solution therewith, the content of cubic $ZrO_2$ crystal increased and the effect of SrO in stabilizing the cubic $ZrO_2$ decreased, thus resulting in lower strength and lower toughness in spite of SrO, $SiO_2$, $TiO_2$ and MgO contained therein.

Through comparison of the results of X-ray diffraction (XRD) analysis of sample No. 1 and sample No. 11, it was confirmed that tetragonal crystal of $ZrO_2$ was stabilized by the addition of SrO in sample No. 1.

FIG. 5 is a Transmission Electron Microscope (TEM) micrograph of the structure of sample No. 1. EDS analysis was conducted for portion a, portion b and portion d of $ZrO_2$ crystal shown in FIG. 3, and a peak of Sr was identified at portion b, thereby confirming that Sr formed a solid solution.

Test of sample No. 10 showed that composition with 65% by weight or less $Al_2O_3$ and 34% by weight or more $ZrO_2$ resulted in characteristics inferior to sample No. 5, such as bending strength of 720 MPa and fracture toughness of 4.3 MPa√m.

In the case of samples Nos. 21 through 27, which were either in short or excess of some of the sintering additives $TiO_2$, MgO and $SiO_2$, sintering temperature became higher and the crystal grains grew large thus resulting in lower bending strength when there was shortage in some of the sintering additives, while much liquid phase component was generated though the sintering temperature remained low thus resulting in lower bending strength when there was an excess in some of the sintering additives.

TABLE 5

| | | | | Sintering additive | | | |
|---|---|---|---|---|---|---|---|
| Sample No. | $Al_2O_3$ % by weight | $ZrO_2$ % by weight | 3YSZ % by weight | SrO % by weight | $TiO_2$ % by weight | MgO % by weight | $SiO_2$ % by weight |
| 1 | 77.8 | 20 | — | 0.7 | 0.5 | 0.3 | 0.7 |
| 2 | 77 | 20 | — | 1.5 | 0.5 | 0.3 | 0.7 |
| 3 | 88.1 | 10 | — | 0.7 | 0.4 | 0.2 | 0.6 |
| 4 | 75.5 | 20 | — | 3 | 0.5 | 0.3 | 0.7 |
| 5 | 68.1 | 30 | — | 0.7 | 0.4 | 0.3 | 0.5 |
| 6 | 78 | 20 | — | 0.9 | 0.3 | 0.4 | 0.4 |
| 7 | 77.6 | 20 | — | 0.8 | 0.5 | 0.4 | 0.7 |
| * 8 | 79.3 | 20 | — | 0.7 | — | — | — |
| 9 | 85.9 | 10 | — | 0.8 | 0.7 | 1.4 | 1.2 |
| * 10 | 58.4 | 40 | — | 0.5 | 0.4 | 0.2 | 0.5 |
| * 11 | 80 | 20 | — | — | — | — | — |
| * 12 | 81.2 | — | 17 | 0.6 | 0.4 | 0.2 | 0.6 |
| 13 | 78.4 | 20 | — | 0.1 | 0.5 | 0.3 | 0.7 |
| 14 | 78.1 | 20 | — | 0.5 | 0.5 | 0.2 | 0.7 |
| 15 | 74.5 | 20 | — | 4 | 0.5 | 0.3 | 0.7 |
| * 16 | 70 | 30 | — | — | — | — | — |
| * 17 | 70 | — | 30 | — | — | — | — |
| * 18 | 80 | — | 20 | — | — | — | — |
| * 19 | 60 | — | 40 | — | — | — | — |
| 20 | 78.4 | 20 | — | 0.5 | 0.4 | 0.2 | 0.5 |
| * 21 | 74.5 | 20 | — | 0.9 | 1 | 1.8 | 1.8 |
| 22 | 75.6 | 20 | — | 1.2 | 0.6 | 1.5 | 1.1 |
| * 23 | 76.7 | 20 | — | 1.1 | 0.2 | 0.7 | 0.8 |
| 24 | 76.7 | 20 | — | 0.9 | 0.8 | 0.4 | 1.2 |
| * 25 | 77.9 | 20 | — | 1 | 0.4 | 0.1 | 0.6 |
| 26 | 76.2 | 20 | — | 0.8 | 0.5 | 0.9 | 1.6 |
| 27 | 76.8 | 20 | — | 1.2 | 0.6 | 1.1 | 0.3 |

* Samples out of the scope of present invention.

TABLE 6

| Sample No. | Solid solution of Sr with $ZrO_2$ | Sintering temperature ° C. | HIP temperature ° C. | Mean grain size of $Al_2O_3$ μm | Mean major axis size of $Al_2O_3$ grains μm | Mean aspect ratio | Mean grain size of $ZrO_2$ μm | Bending strength MPa | Fracture toughness MPa√m | Hardness Hv | Specific wear $mm^2/N$ ($\times 10^{-10}$) |
|---|---|---|---|---|---|---|---|---|---|---|---|
| 1 | Present | 1350 | 1300 | 0.5 | 0.7 | 1.6 | 0.3 | 1490 | 5.4 | 1790 | 0.16 |
| 2 | Present | 1400 | 1300 | 0.7 | 1.4 | 2.1 | 0.4 | 1540 | 5.4 | 1780 | 0.11 |
| 3 | Present | 1400 | 1300 | 0.8 | 1.5 | 2.1 | 0.3 | 1390 | 4.2 | 1820 | 0.03 |
| 4 | Present | 1500 | 1400 | 1 | 1.8 | 2.5 | 0.7 | 1210 | 5.6 | 1590 | 0.22 |
| 5 | Present | 1400 | 1300 | 0.7 | 1.6 | 1.8 | 0.5 | 1340 | 5.7 | 1530 | 0.2 |
| 6 | Present | 1350 | 1300 | 0.5 | 0.7 | 1.6 | 0.3 | 1410 | 5.4 | 1740 | 0.15 |
| 7 | Present | 1350 | 1300 | 0.5 | 0.7 | 1.6 | 0.3 | 1270 | 5.4 | 1720 | 0.13 |
| * 8 | No | 1450 | 1350 | 0.8 | 1.4 | 1.8 | 0.5 | 1120 | 4.5 | 1790 | 0.23 |
| 9 | Present | 1400 | 1300 | 0.8 | 1.5 | 2.1 | 0.3 | 1220 | 4.2 | 1840 | 0.07 |
| * 10 | Present | 1400 | 1300 | 0.7 | 1.4 | 2.1 | 0.4 | 720 | 4.3 | 1540 | 0.74 |
| * 11 | No | 1400 | 1300 | 0.8 | 0.8 | 1 | 0.4 | 930 | 3.3 | 1720 | 0.55 |
| * 12 | No | 1400 | 1300 | 0.7 | 1.4 | 2.1 | 0.4 | 830 | 3.2 | 1830 | 0.42 |
| 13 | Present | 1350 | 1300 | 0.5 | 0.6 | 1.3 | 0.3 | 1120 | 4 | 1790 | 0.12 |

TABLE 6-continued

| Sample No. | Solid solution of Sr with ZrO$_2$ | Sintering temperature °C. | HIP temperature °C. | Mean grain size of Al$_2$O$_3$ μm | Mean major axis size of Al$_2$O$_3$ grains μm | Mean aspect ratio | Mean grain size of ZrO$_2$ μm | Bending strength MPa | Fracture toughness MPa√m | Hardness Hv | Specific wear mm$^2$/N (×10$^{-10}$) |
|---|---|---|---|---|---|---|---|---|---|---|---|
| 14 | Present | 1350 | 1300 | 0.5 | 0.7 | 1.6 | 0.3 | 1470 | 5.1 | 1790 | 0.15 |
| 15 | Present | 1450 | 1350 | 0.8 | 1.8 | 2.3 | 0.5 | 1050 | 5.8 | 1520 | 0.28 |
| *16 | No | 1400 | 1300 | 0.9 | 1 | 1.1 | 0.5 | 800 | 3.5 | 1550 | 0.71 |
| *17 | No | 1400 | 1300 | 0.9 | 0.9 | 1 | 0.5 | 1330 | 3.3 | 1550 | 0.66 |
| *18 | No | 1500 | 1400 | 1.3 | 1.5 | 1.1 | 0.7 | 990 | 3.1 | 1830 | 0.45 |
| *19 | No | 1400 | 1300 | 0.9 | 0.9 | 1 | 0.7 | 1390 | 3.5 | 1570 | 1.22 |
| 20 | Present | 1400 | 1350 | 0.7 | 1.4 | 2.1 | 0.4 | 1290 | 5.1 | 1740 | 0.14 |
| *21 | Present | 1350 | 1300 | 0.5 | 0.7 | 1.6 | 0.3 | 990 | 4.2 | 1710 | 1.66 |
| 22 | Present | 1350 | 1300 | 0.5 | 0.7 | 1.6 | 0.3 | 1010 | 4.5 | 1720 | 0.51 |
| *23 | Present | 1500 | 1350 | 1.1 | 1.8 | 1.6 | 0.7 | 970 | 4.1 | 1730 | 0.44 |
| 24 | Present | 1400 | 1350 | 0.7 | 1.4 | 2.1 | 0.4 | 980 | 4.2 | 1740 | 0.29 |
| *25 | Present | 1500 | 1350 | 1.1 | 1.8 | 1.6 | 0.7 | 940 | 4.4 | 1730 | 0.43 |
| 26 | Present | 1400 | 1350 | 0.7 | 1.4 | 2.1 | 0.4 | 990 | 4.2 | 1740 | 0.28 |
| 27 | Present | 1500 | 1350 | 1.2 | 1.8 | 1.5 | 0.7 | 950 | 4.3 | 1730 | 0.37 |

* Samples out of the scope of present invention.

According to the present invention, a biomedical member having very high strength and high toughness and an artificial joint can be provided.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description but is only limited by the scope of the appended claims.

The invention claimed is:

1. A biomedical member formed from a composite ceramic including: an alumina phase; and a zirconia crystal phase,
   wherein a mean grain size of said zirconia crystal phase is 0.5 μm or smaller;
   wherein said biomedical member contains at least one selected from the group consisting of a metal phase and a metal oxide, and sintering additives;
   wherein said metal phase is at least one selected from the group consisting of molybdenum, tungsten and a mixture of molybdenum and tungsten;
   wherein said metal oxide is at least one selected from the group consisting of strontium oxide and yttrium oxide;
   wherein 65 to 96% by weight of said alumina phase is contained in said biomedical member;
   wherein 4 to 34.4% by weight of said zirconia crystal phase is contained in said biomedical member;
   wherein said sintering additives contain 0.20% by weight or more silicon oxide, 0.22% by weight or more titanium oxide and 0.12% by weight or more magnesium oxide, while the total amount of silicon oxide, titanium oxide and magnesium oxide is in a range from 0.6 to 4.5% by weight.

2. The biomedical member according to claim 1, wherein a mean grain size of aluminum oxide of said alumina phase is 3 μm or smaller.

3. The biomedical member according to claim 1, wherein 70% or more of zirconium oxide of said zirconia crystal phase is tetragonal crystal.

4. The biomedical member according to claim 1, wherein an atomic ratio Titanium/Magnesium of titanium oxide and magnesium oxide is in a range from 0.5 to 1.2.

5. The biomedical member according to claim 1, wherein at least a part of the titanium oxide and magnesium oxide is dissolved in an aluminum oxide crystal so as to form a solid solution crystal, and the total amount of these materials dissolved is 0.1% by weight or more off said aluminum oxide.

6. The biomedical member according to claim 1, wherein oxides of at least one of titanium and magnesium or composite oxide grains containing said oxides are dispersed in at least a part of said aluminum oxide crystal grains.

7. The biomedical member according to claim 1, wherein specific wear of the sintered ceramics of said composite ceramic is 0.3×10$^{10}$ mm$^2$/N or less after being subjected to accelerated aging test conducted in saturated water vapor of 121° C. for 152 hours.

8. A biomedical member formed from a composite ceramic including: an alumina phase; and a zirconia crystal phase,
   wherein a mean grain size of said zirconia crystal phase is 0.5 μm or smaller;
   wherein said biomedical member contains at least one selected from the group consisting of a metal phase and a metal oxide, and sintering additives;
   wherein said metal phase is at least one selected from the group consisting of molybdenum, tungsten and a mixture of molybdenum and tungsten;
   wherein said metal oxide is at least one selected from the group consisting of strontium oxide and yttrium oxide;
   wherein said biomedical member includes 65% by weight or more of said alumina phase, 4 to 34% by weight of said zirconia phase and 0.1 to 4% by weight of strontium oxide, while strontium forms a solid solution with part of said zirconium oxide grains;
   wherein said sintering additives comprise titanium oxide, magnesium oxide and silicon oxide.

9. The biomedical member according to claim 8, wherein said composite ceramics contains 0.20% by weight or more silicon oxide, 0.22% by weight or more titanium oxide and 0.12% by weight or more magnesium oxide, while the total amount of silicon oxide, titanium oxide and magnesium oxide is in a range from 0.6 to 4.5% by weight.

10. The biomedical member according to claim 8, wherein the aluminum oxide grains in said composite ceramics have elongated shape observed in SEM image, mean value of the largest dimensions of said aluminum oxide grains, namely the size along major axis thereof, is 1.5 μm or smaller, aspect ratio that is the ratio of the major axis size to the minor axis size of the aluminum oxide grains, namely the size along the direction perpendicular to the major axis, is 2.5 or less and a median value between the mean minor axis size and mean major axis size is 1 μm or less.

11. A method for producing a biomedical member that is formed from a composite ceramic including an alumina phase and a zirconia crystal phase and contains a metallic component, wherein said metallic component is at least one selected from the group consisting of molybdenum, tungsten and a mixture of molybdenum and tungsten, or a metal oxide phase, wherein said metal oxide phase is at least one selected from the group consisting of strontium oxide and yttrium oxide, and sintering additives, comprising mixing raw materials that contain aluminum, zirconium, silicon, titanium, magnesium in the form of metals or compounds of metals so that the mixture of the raw materials contains 0.20% by weight or more silicon oxide, 0.22% by weight or more titanium oxide and 0.12% by weight or more magnesium oxide while the total amount of silicon oxide, titanium oxide and magnesium oxide is in a range from 0.6 to 4.5% by weight, when contents of the metals or the compounds of the metals are converted to the contents of metal oxides, forming the mixture into a compact in a predetermined shape and sintering the compact at a temperature in a range from 1300 to 1500° C. thereby to obtain a sintered ceramic.

12. The method for producing the biomedical member according to claim 11, which comprises sintering the compact at a temperature in a range from 1300 to 1500° C. in the oxidizing atmosphere, and heat treating the sintered ceramic at a temperature at least 60° C. lower than the sintering temperature in a reducing atmosphere.

13. The method for producing the biomedical member according to claim 11, further comprising applying hot isostatic treatment at a temperature at least 30° C. lower than said sintering temperature, after sintering.

* * * * *